United States Patent [19]

Jessel, Jr. et al.

[11] Plant 4,667

[45] Mar. 10, 1981

[54] CARNATION PLANT

[75] Inventors: Walter H. Jessel, Jr., Fremont; William E. Duffett, Salinas, both of Calif.

[73] Assignee: Yoder Brothers, Inc., Barberton, Ohio

[21] Appl. No.: 89,730

[22] Filed: Oct. 31, 1979

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Schwartz, Jeffery, Schwaab, Mack, Blumenthal & Koch

[57] ABSTRACT

A carnation plant known by the cultivar name Ace and particularly characterized as to uniqueness by the combined characteristics of commercial double flower type; flat flower form, reflexing slightly at maturity; medium flower size; light orange flower color with scarlet red picotee color pattern, faintly striped; medium flowering response; 6 to 8 flowers and buds showing color per flower stem; medium peduncle length; strong peduncle strength; and tall plant height.

2 Drawing Figures

1

The present invention comprises a new and distinct cultivar of *Dianthus caryophyllus*, L., hereinafter referred to by the name Ace.

Ace is the product of a planned breeding program which had the objective of creating new spray type carnation cultivars in a wide color range with fast flowering response, unrestricted breaking action, vigorous growth, strong non-brittle stems, high bud and flower count, and attractive, durable flowers for year-round commercial production.

Ace was originated from a cross made in Barberton, Ohio in the year 1973. The male parent was Red Baron (unpatented; commercially available). The female parent was Orange Elf (unpatented; commercially available). Ace was discovered and selected as one flowering plant within the progeny of the stated parentage by Walter H. Jessel, Jr. and William E. Duffett on Aug. 28, 1974 in a controlled environment in Barberton, Ohio.

The first act of asexual reproduction of Ace was accomplished when vegetative cuttings were taken from the initial selection in April, 1975 in a controlled environment in Barberton, Ohio by a technician working under formulations established and supervised by Walter H. Jessel, Jr. and William E. Duffett. Horticultural examination of selected units initiated June 13, 1977 has demonstrated that the combination of characteristics as herein disclosed for Ace are firmly fixed and are retained through successive generations of asexual reproduction.

Ace has not been observed under all possible environmental conditions. The phenotype may vary significantly with variations in environment such as temperature, light intensity, and daylength. The following observations, measurements, and comparisons describe plants grown in Barberton, Ohio and Salinas, Calif. under greenhouse conditions which approximate those generally used in commercial practice.

The following traits have been repeatedly observed and are determined to be basic characteristics of Ace which in combination distinguish this carnation as a new and distinct cultivar:

(1) Commercial double flower type.

(2) Flat flower form, reflexing slightly at maturity.

(3) Medium flower size, ranging from 45 to 65 mm. in diameter.

2

(4) Light orange flower color with scarlet red picotee color pattern, faintly striped.

(5) Medium flowering response.

(6) 6 to 8 flowers and buds showing color per flowering stem.

(7) Medium peduncle length, ranging from 10 to 12 cm.

(8) Strong peduncle strength.

(9) Tall plant height.

The accompanying photographic drawings show typical inflorescence and foliage characteristics of Ace. Sheet 1 is a color photograph of a flower stem of Ace, with colors being as nearly true as possible with illustrations of this type. Sheet 2 is a black and white photograph of three views of the flower of Ace.

Of the several commercially available carnations known to the present inventors, the most similar in comparison to Ace are the parental cultivars, Orange Elf and Red Baron. Reference is made to Chart A which compares certain characteristics of Ace with those same characteristics of Orange Elf and Red Baron. General comparisons are as follows:

(1) In comparison to Orange Elf, Ace has less pronounced striping in the flower color pattern, smaller flower size, more buds and flowers per stem, shorter peduncle length, greater peduncle strength, and shorter plant height. The flower color and flowering response period of Ace are similar to those same characteristics of Orange Elf.

(2) In comparison to Red Baron, Ace has different flower color, different flower color pattern, shorter flowering response period, and less brittle peduncles. The flower size, number of buds and flowers, peduncle length, and plant height of Ace are similar to those same characteristics of Red Baron.

In the following description, color references are made to The Limit Color Cascade, by the Munsell Company, 1972 edition. The color values determined between 4:00 P.M. and 4:30 P.M. on June 13, 1977 under 150 foot-candle light intensity at Barberton, Ohio are denoted by (a). Color values determined between 8:00 A.M. and 8:30 A.M. on Dec. 12, 1978 under 100 foot-candle light intensity at Salinas, Calif., are denoted by (b).

Classification:

*Botanical.*—*Dianthus caryophyllus,* L. Ace

*Commercial.*—Spray carnation for cut flower production.

Inflorescence characteristics:

*Flowering response.*—Medium, ranging from 22 weeks (at Salinas, Calif. grown pinched from a June 1 plant date) to 30 weeks (at Barberton, Ohio grown pinched from a November 1 plant date).

*Inflorescence type.*—Semi-compound spray, with 1 to 4 buds per lateral; rarely seen as a terminal spray.

*Number of buds and flowers per stem.*—6–8 showing color on first cut.

*Peduncle length.*—Medium, ranging from 10 to 12 cm. on top flower.

*Peduncle strength.*—Strong, holding flowers erect in all periods; seldom brittle.

*Flower.*—Size: Medium, 45 to 65 mm. in diameter when grown as a spray; too small for adaption as a commercial disbud. Type: Commercial double, petals from 25 to 30 in number. Form: Flat, slightly reflexed at maturity.

*Corolla color.*—General tonality from a distance of 3 meters: 38-6 at petal margin over 34-2 (a,b). Abaxial: 38-8(a,b) in picotee and striped pattern over 34-3(a) to 34-2(b) (immature), to 38-6(a,b) in picotee and striped pattern over 32-2(a) to 34-2(b) (mature). Adaxial: 38-7(a,b) in faint picotee pattern over 32-2(a) to 33-2(b).

*Keeping quality.*—On plant, up to 18 days; as a cut flower, up to 15 days under room temperature of 20° C.

*Fragrance.*—Slight to none; typical carnation.

*Reproductive organs.*—Androecium: Typical carnation, normal to semi-petaloid; medium filament length; moderate pollen. Gynoecium: Typical carnation, normal in all respects; white pistil of short length, ranging from 15 to 18 mm.

Plant characteristics:

*Growth and duration.*—Bushy and vigorous semi-erect perennial; typical of cultivars adaptable to commercial cut spray production; similar to that of Red Baron.

*Branching pattern.*—Semi-erect, numerous and unrestricted at base of plant.

*Height.*—Tall, 80 to 85 cm. at time of first cut on a pinched plant; similar to that of Red Baron.

Stem.—Strong, with bend of 10 to 15 degrees (Society of American Florist's Standards), seldom brittle; approximately 50 to 55 cm. in length from top to first vegetative lateral.

*Foliage.*—Occurrence: Abundant, typical carnation; similar to that of Red Baron. Color (Abaxial): Approximately 21-14 to 21-15 (a,b), but more greyed. Color (Adaxial): Approximately 20-13 to 20-14 (a,b), but more greyed.

CHART A

COMPARISON OF ACE, ORANGE ELF, AND RED BARON

| CULTIVAR | FLOWER COLOR | FLOWER COLOR PATTERN | FLOWER SIZE | NUMBER OF BUDS AND FLOWERS/-STEM |
|---|---|---|---|---|
| ACE | Light Orange & Scarlet Red | Picotee, faintly striped | Medium, 45 to 65 mm | 6 to 8 |
| ORANGE ELF | Light Orange & Scarlet Red | Picotee, darkly striped | Large 75 to 85 mm | 4 to 5 |
| RED BARON | Scarlet Red to Brick Red | Solid | Medium, 45 to 65 mm | 6 to 8 |

| CULTIVAR | FLOWERING RESPONSE PERIOD | PEDUNCLE LENGTH | PEDUNCLE STRENGTH | PLANT HEIGHT |
|---|---|---|---|---|
| ACE | Medium, from 22 to 30 weeks | Medium, 10 to 12 cm | Strong | Tall, 80 to 85 cm |
| ORANGE ELF | Medium, from 22 to 30 weeks | Very Long, 18 to 20 cm | Weak | Very Tall 95 to 100 cm |
| RED BARON | Slow, from 25 to 34 weeks | Medium, 10 to 12 cm | Strong, almost brittle | Tall, 80 to 85 cm |

Comparison made of pinched, flowering plant grown in Salinas, California

We claim:

1. A new and distinct cultivar of *Dianthus caryophyllus,* L., known by the cultivar name Ace, as described and illustrated, and particularly characterized as to uniqueness by the combined characteristics of commercial double flower type; flat flower form, reflexing slightly at maturity; medium flower size, ranging from 45 to 65 mm. in diameter; light orange flower color with scarlet red picotee color pattern, faintly striped; medium flowering response; 6 to 8 flowers and buds showing color per flowering stem; medium peduncle length, ranging from 10 to 12 cm.; strong peduncle strength; and tall plant height.

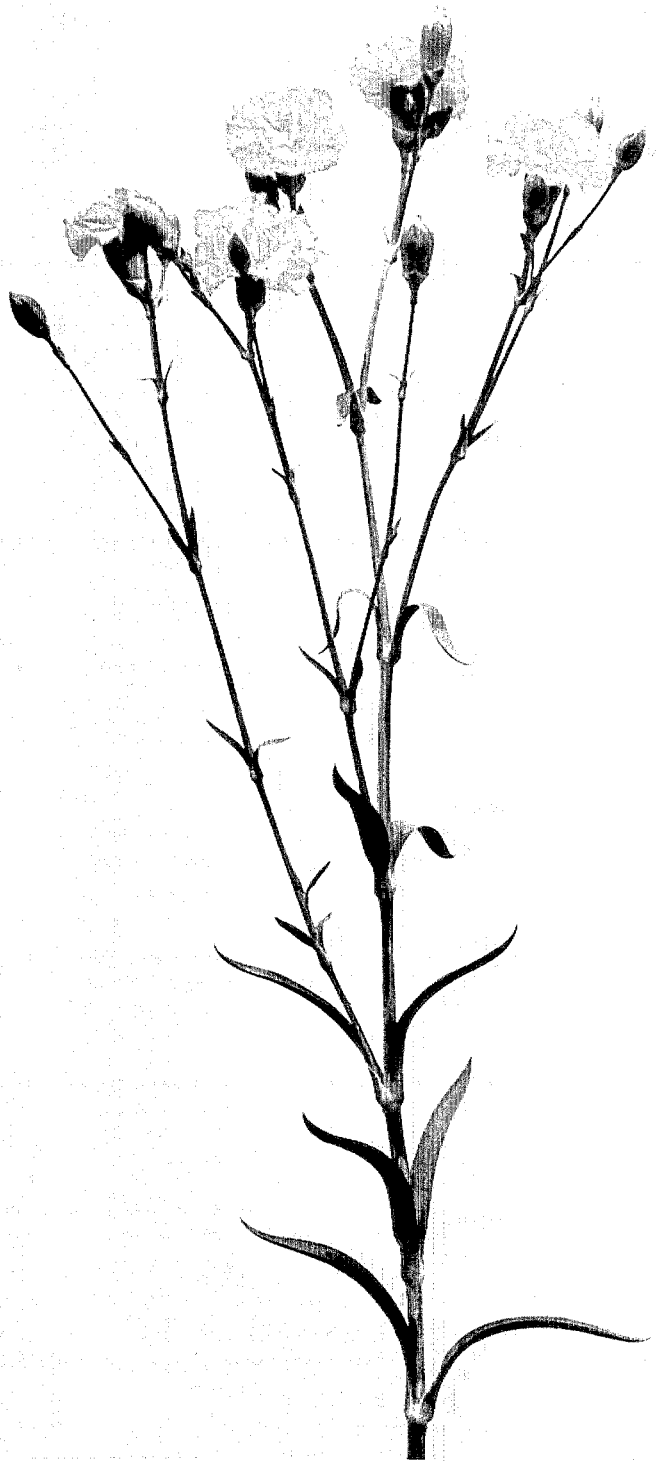

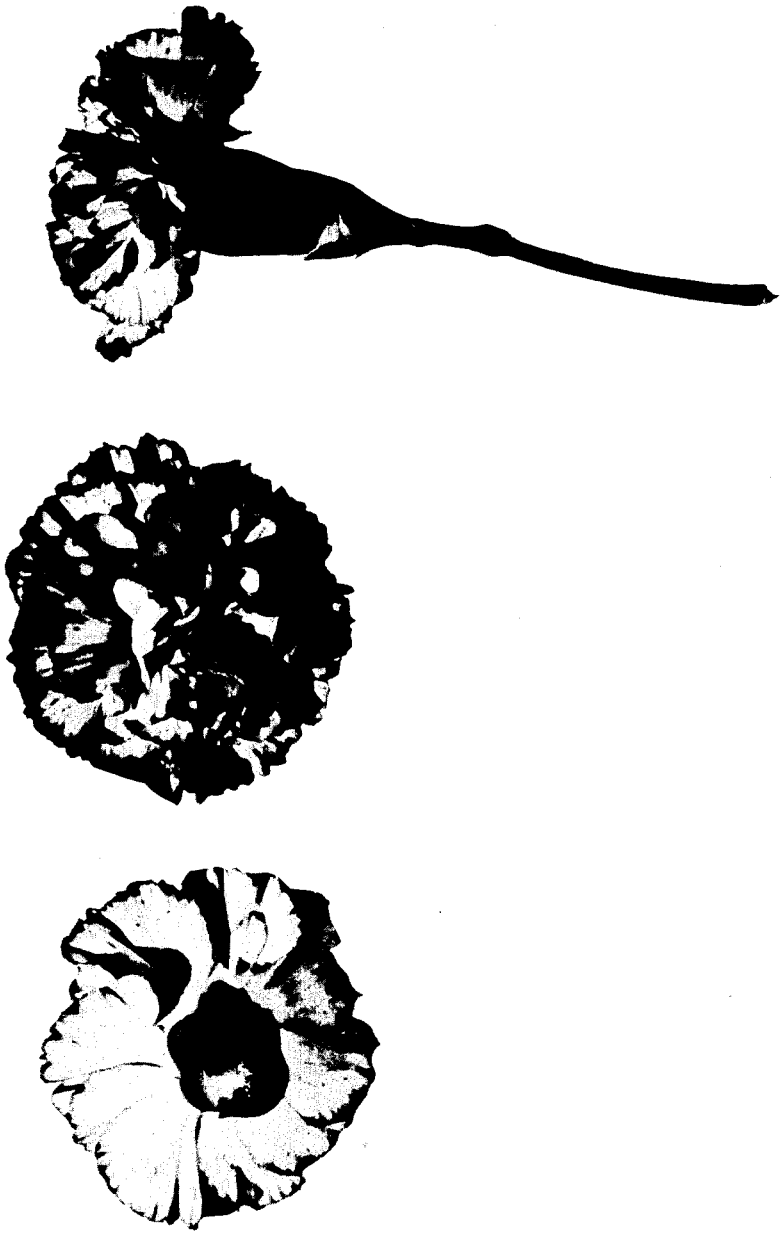

* * * * *